United States Patent [19]

Freire et al.

[11] Patent Number: 5,707,149
[45] Date of Patent: Jan. 13, 1998

[54] DEVICE AND METHOD FOR MEASURING THE HEAT OF REACTION RESULTING FROM MIXTURE OF A PLURALITY OF REAGENTS

[75] Inventors: Ernesto Freire; George P. Privalov; Peter L. Privalov; Vincent V. Kavina, all of Baltimore, Md.

[73] Assignee: Johns Hopkins University, Baltimore, Md.

[21] Appl. No.: 534,699

[22] Filed: Sep. 27, 1995

[51] Int. Cl.[6] .................................................. G01K 17/00
[52] U.S. Cl. ........................... 374/33; 374/31; 422/51; 436/147
[58] Field of Search .......................... 374/31, 33, 34, 374/36; 422/51; 436/147

[56] References Cited

U.S. PATENT DOCUMENTS 3,716,333  2/1973  Peuschel .
5,482,679  1/1996  Dijkstra et al. .................. 374/36 X

*Primary Examiner*—Richard Chilcot
*Assistant Examiner*—Joseph L. Felber
*Attorney, Agent, or Firm*—Cushman Darby & Cushman Intellectual Property Group of Pillsbury Madison & Sutro, LLP

[57] ABSTRACT

A method for measuring the heat of reaction resulting from the mixture of a plurality of reagents comprising the steps of providing a first reagent into a compartment; providing a second reagent into the compartment so as to mix the second reagent with the first reagent within the compartment; withdrawing a predetermined amount of the mixed first and second reagents from the compartment; depositing the withdrawn predetermined amount of the mixed first and second reagents back into the compartment; generating electrical signals based on the heat of reaction of the mixed first and second reagents; and deriving data indicative of the heat of reaction based on the electrical signals.

18 Claims, 5 Drawing Sheets

DEVICE AND METHOD FOR MEASURING THE HEAT OF REACTION RESULTING FROM MIXTURE OF A PLURALITY OF REAGENTS

BACKGROUND OF THE INVENTION

The present invention relates to a device and method for measuring the heat of reaction resulting from the mixture of a plurality of liquid reagents.

The heat of reaction is one of the most important thermochemical characteristics of any reaction and is widely used in fundamental research and applied studies, since it contains the main information on the energetics of a chemical reaction under study. Direct colorimetric measurements of the heats of reaction of liquid reagents are of special importance in chemistry, biochemistry, molecular biology, biotechnology, and pharmacology. Until today, however, the use of reaction calorimetry has been limited by the relatively low sensitivity of existing instruments.

Most of the important biochemical preparations are available in very small amounts and are extremely expensive. Also, in many cases, biochemical reactions exhibit extremely high molecular affinities characterized by association constants ($K_a$) larger than $10^9 M^{-1}$ which force the researcher to work under very dilute conditions. These circumstances have led throughout the years to several attempts to develop calorimeters with higher sensitivity.

Usually, for a complete thermochemical description of a reaction, one needs the knowledge of the heats of reaction across a broad range of reactant concentrations. This is achieved using special reaction calorimeters, known as titration calorimeters, which permit measurement of the heat effects upon titration of one reagent by another reagent. At the present time, only one known titration calorimeter, that manufactured by Microcal Inc., has the ability to measure heats of reaction as small as 1 μcal. Even though the sensitivity of this instrument is much higher than that of older instruments, it is still not adequate to measure high affinity biochemical reactions.

The main purpose of the present invention is to provide an instrument for calorimetric titration that is easier to operate, more reliable, precise, and of higher sensitivity. This instrument will permit a direct calorimetric determination of binding isotherms for biochemical associations with $K_a > 10^9 M^{-1}$.

One of the most complicated problems in precision reaction calorimetry of liquids, and particularly in titration microcalorimetry, is the problem of mixing the reagents. The mixing should be precise, complete, and permit to take into account the Joule effect of mixing, i.e., the heat effect produced by the mechanical work upon mixing.

Usually, mixing is achieved in two stages: in the first stage a certain amount of one reagent is introduced into a certain amount of the other reagent; in the second stage, both reagents are stirred by shaking or by the action of a mechanical stirrer.

The disadvantage of shaking is that it is impossible to shake a small amount of liquid efficiently enough to achieve rapid, thorough mixing, and that it introduces mechanical heat into the mixture which is not easy to control. In instruments using this method of mixing and stirring, the two reactants have an open surface in contact with the gas phase (air). This is not always appropriate, since it often leads to the production of bubbles, which introduce significant noise into the observed heat effect of mixing. More modern titration calorimeters abandoned this method in favor of a continuously rotating mechanical stirrer.

There are numerous disadvantages of using a mechanical stirrer, however. First, it produces a continuous Joule heat effect which results in a baseline shift in the measured heat of reaction. Second, if the mechanical stirrer is not perfectly aligned, significant levels of noise are produced that limit the effective sensitivity of the instrument. Third, the presence of the stirring paddle inside the solution limits the ability to miniaturize the calorimetric cell. Fourth, because the stirrer is in contact with the reagents and the outside environment, it offers a heat conduction path that adversely affects the performance of experiments at temperatures other than ambient temperature. Fifth, proper adjustment of the stirrer requires a certain degree of experience and qualification and is a source of added complication to experimentation. Finally, because the stirrer displaces a certain volume from the reactor cell, such volume must be known very precisely and must be reproducible from experiment to experiment.

Another problem associated with conventional calorimeters is the necessity of using water baths and water circulators in order to control the temperature of the calorimeter. The need for such components limits the ability to miniaturize the device and the ability to make the device portable.

SUMMARY OF THE INVENTION

It is an object of the present invention to provide a method that eliminates the problems associated with use of the mechanical stirrer, the need to shake during reaction microcalorimetry, and the need to use a circulating water bath in a microcalorimetric instrument.

To accomplish this object, the present invention provides a method for measuring the heat of reaction resulting from the mixture of a plurality of reagents, which method comprises the steps of providing a first liquid reagent into a compartment; providing a second reagent into the compartment so as to mix the second liquid reagent with the first reagent within the compartment; withdrawing a predetermined amount of the mixed first and second reagents from the compartment; depositing the predetermined amount of the mixed first and second reagents that has been withdrawn from the compartment back into the compartment; generating an electrical signal based on the heat of reaction of the mixed first and second reagents; and deriving data indicative of the heat of reaction based on the electrical signal.

It is a further object of the present invention to provide a device which overcomes the above-noted problems. In accomplishing this object, the present invention provides a device for measuring the heat of reaction resulting from mixture of a plurality of reagents, comprising: a compartment adapted to initially contain at least a first reagent; an injection assembly for providing a second reagent into the compartment to permit the first and second reagents to initially mix within the compartment, the injection assembly being constructed and arranged to be able to i) withdraw a predetermined portion of the first and second reagents from the compartment after the reagents have been initially mixed within the compartment and ii) deposit the withdrawn predetermined portion of the first and second reagents back into the compartment so as to facilitate stirring of the first and second reagents within the compartment; and a measuring apparatus operably connected with the compartment for deriving data indicative of the heat of reaction resulting from mixing the first and second reagents.

It is a further object of the invention to provide a method wherein the step of providing the second reagent into the compartment causes some displacement of the first reagent within the compartment.

It is a further object of the invention to provide or inject a reagent into a calorimetric compartment in such fashion that the reagents circulate in a substantially uniform fashion within the compartment so as to facilitate stirring and complete mixing of reagents within the compartment.

These and other objects of the present invention will become more apparent during the course of the following detailed description of the appended drawings.

DETAILED DESCRIPTION OF THE DRAWINGS

The present invention operates under the principle that two liquid reagents will be mixed quickly and efficiently if one of the reagents is introduced into the other with sufficient speed and turbulence. Therefore, in the present invention, the mechanical energy necessary for mixing is derived from the impulse generated by the rapid but controlled introduction of a second reagent into the calorimetric reaction cell already containing a first reagent. Stirring is accomplished either by injecting an additional amount of the first reagent or by withdrawing a portion of the mixed first and second reagents within the cell and reinjecting it into the cell. Additional stirring may be accomplished by successive withdrawal and immediate reintroduction of a small fraction of the total cell volume. To effectively accomplish stirring, the injected reagent or injected mixed reagents should be in the form of a high-velocity jet stream. The jet stream should be precisely calibrated in velocity and volume, and be directed so as to produce turbulent, circular flow in the reactor to cause the reagents to mix quickly and completely.

The efficiency of mixing depends, in part, on the construction of the reactor—its geometry, volume, and orientation of the jet injection devices. The ultimate sensitivity and accuracy of the entire calorimetric instrument also depends on these elements and may also be influenced by other factors, such as the construction of the calorimeter cell or compartment, inlets and outlets to and from the cell, thermostation for maintaining the compartment at a relatively constant temperature, sensors, injection devices for the injection of reagents at the desired volume and speed, and the automatization of the measuring process.

Figure 1:
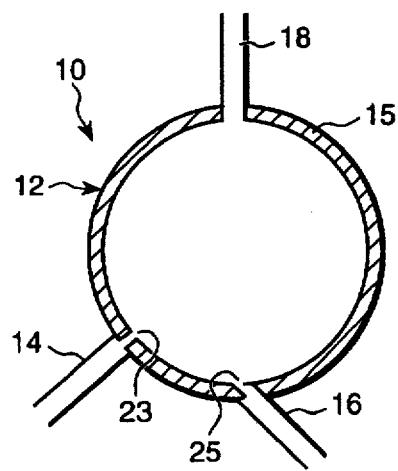
FIG. 1 is a sectional front view of a calorimetric reactor in accordance with the principles of the present invention.
Figure 2:
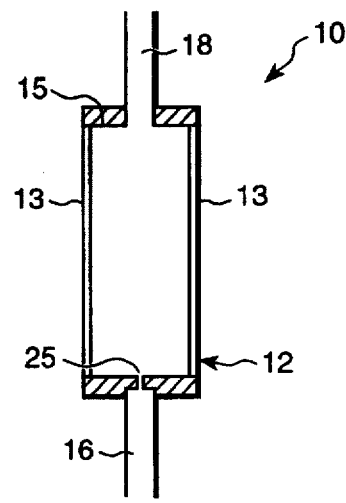
FIG. 2 is a sectional side view of the calorimetric reactor of the present invention.

FIGS. 1 and 2 are schematic representations of a calorimetric reactor, generally indicated at 10, manufactured in accordance with the principles of the present invention. The reactor 10 includes a main compartment in the form of a thin cylindrical cell or compartment 12, made from a chemically inert metal, such as gold or stainless steel, or other material that is chemically inert and of high thermal conductivity. Cell 12 has circular end walls 13, as shown in FIG. 2, and a peripheral rim 15 defining its generally cylindrical shape. These end walls 13 preferably have a diameter greater than the distance therebetween. For example, the cell's volume is preferably between 0.3–1.5 ml, with a typical diameter of the circular end walls 13 being approximately between 20–25 mm, and a typical distance between the circular end walls 13 being approximately 2–3 mm. The cell 12 has two inlet tubes, including a radial inlet tube 14 and a tangential inlet tube 16, and one outlet tube 18. The tubes 14, 16 and 18 are made from a chemically inert material having a relatively low thermal conductivity, such as platinum, TEFLON (polytetrafluorethylene), or stainless steel. The inner diameter of the tubes is preferably between about 0.5–1.0 mm. The tubes are welded or otherwise rigidly connected with the rim 15. The assembly is preferably constructed and arranged such that the circular end walls 13 are vertically disposed, the outlet tube 18 is connected at the top of the rim 15, the tangential inlet tube 16 is connected at the bottom of the rim 15, and the radial inlet tube 14 is connected at the side of the rim. This arrangement facilitates evacuation of the liquid from the cell, washing of the cell, and refilling of the cell with new reagent. Preferably, a calibration heater (not shown) used for calibrating the instrument is also located at the rim of the cell.

Figure 6:
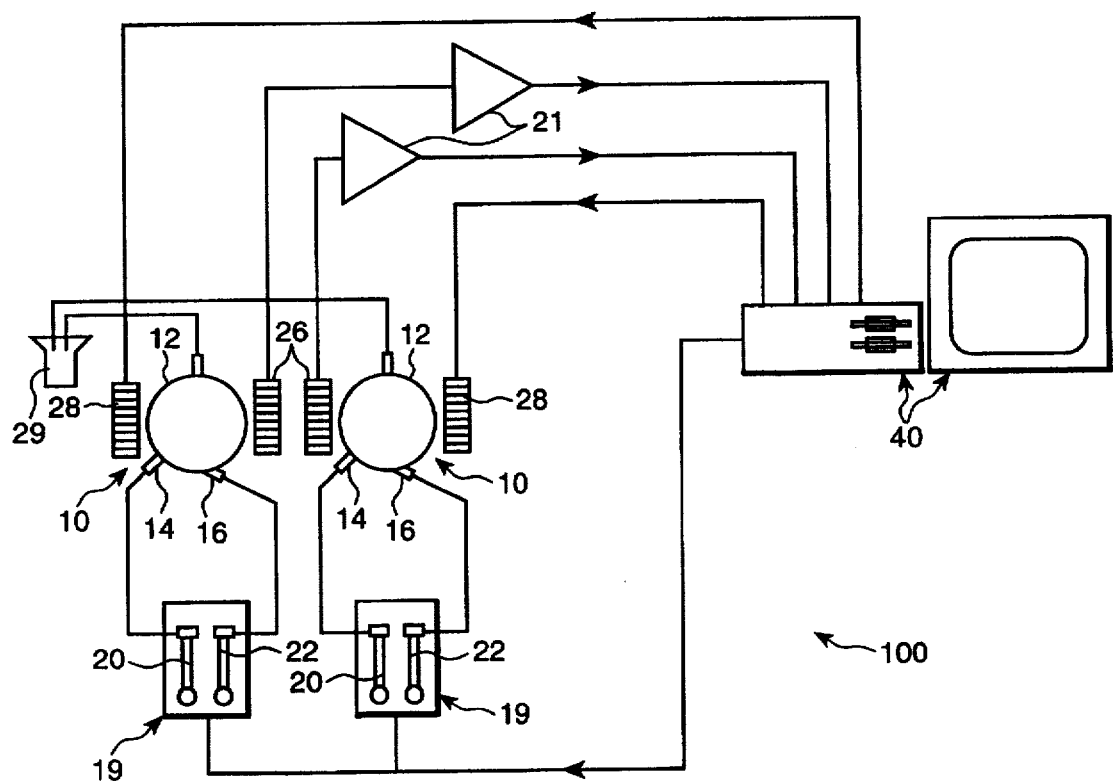
FIG. 6 is a schematic representation of a computer-controlled differential titration calorimeter assembly in accordance with the principles of the present invention.

As shown in conjunction with the computer-controlled calorimeter assembly 100 of FIG. 6 (which utilizes two reactors), each reactor 10 is connected with an injector apparatus, generally indicated at 19, which includes a pair of injection devices 20 and 22, for introducing the two reagents into the cell 12 and for achieving high efficiency mixing of the reagents within the cell. It can be appreciated that inlet tubes 14 and 16 provide a conduit through which injection devices 20 and 22, respectively, are in fluid communication with the cell 12. More specifically, the rim 15 is provided with a pair of holes 23 and 25, preferably about 0.1–0.2 mm in diameter, which permit the inlet tubes 14 and 16, respectively, to communicate with the cell 12. The outlet tube 18, on the other hand connects the cell 12 with a drain or collection tube (shown as reference numeral 29 in FIG. 6) for disposal of the mixed reagents. Each injection device together with its respective inlet tube can be considered as being a single injection assembly. Thus, each cell or compartment 12 can be considered to be connected to a first injection assembly (e.g., 14, 20) and a second injection assembly (e.g., 16, 22).

Injection devices 20 and 22, as shown in FIG. 6, are capable of injecting liquid into cell 12, via inlet tubes 14 and 16, with a controlled speed and volume, and are commercially available, for example, from Hamilton Inc. (model 940). They are each in the form of an electrically operated automatic syringe assembly with a mechanical piston/cylinder arrangement that is capable of injecting and withdrawing the reagents to and from the cell 12. Injection device 20, which is connected with the radially oriented inlet tube 14, operates to shoot a jet radially towards the center of cell 12 and is used for injecting the titrating reagent into the cell. The injection device 22, on the other hand, is connected with the tangentially oriented inlet tube 16 and operates to shoot a jet generally tangentially with respect to the cell. The tangential injection device 22 allows repeated withdrawal and reinjection of a fraction of the total cell volume through tangential inlet tube 16 and is used for additional steering of the reagents after they are initially provided into the cell. The tangential disposition of tube 16 is highly preferred as it creates a turbulent, circular flow of mixed reagents in a uniform direction within the cell that causes rapid and complete mixing.

Figure 3:
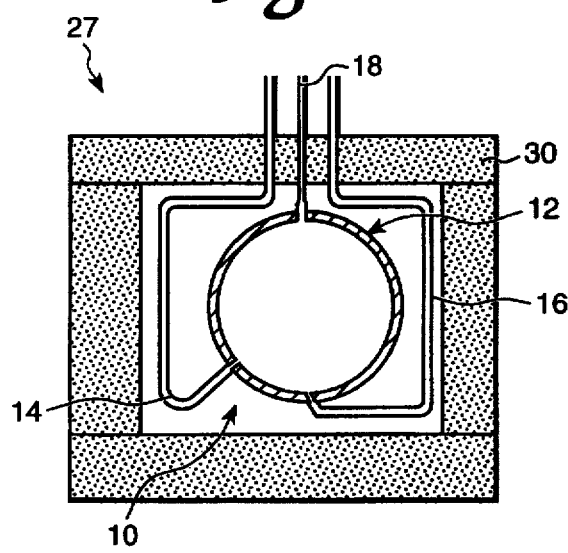
FIG. 3 is a sectional front view of a calorimetric reactor assembly including a reaction cell as shown in FIG. 1 in accordance with the principles of the present invention.
Figure 4:
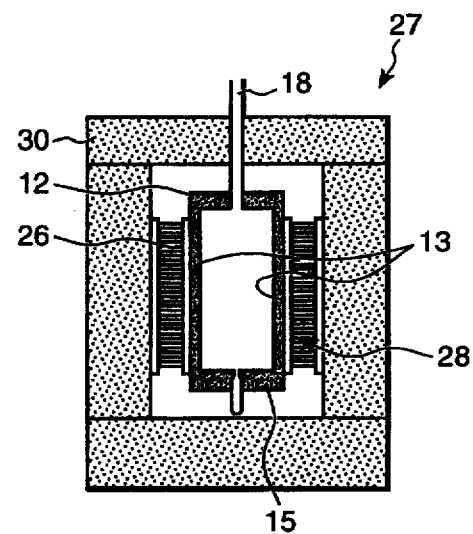
FIG. 4 is a sectional side view of the calorimetric reactor assembly of FIG. 3.

FIGS. 3 and 4 show a calorimetric reactor assembly 27 incorporating a reactor 10 as described in conjunction with FIGS. 1 and 2. From FIGS. 3 and 4, it can be appreciated that the cell 12 is squeezed or compressed between two conventional semiconductor thermopiles, including a measuring thermopile 26 and a compensating thermopile 28, which make good thermal contact with the exterior surfaces of the opposite flat circular walls 13 of the cell. The thermopiles, in turn, are each compressed between the cell 12 and a surrounding thermostated block 30. The thermostated block 30, preferably made of solid copper, makes good thermal contact with sides of the thermopiles and is maintained at a constant temperature. The thermostated block 30 defines a symmetrical surrounding for the cell.

Figure 5:
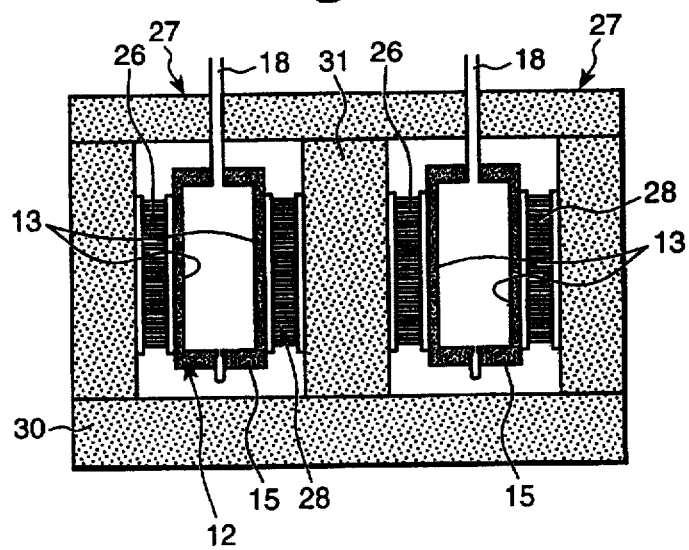
FIG. 5 is a sectional side view of a dual differential calorimetric reactor assembly comprising two reactor cells in accordance with the principles of the present invention.

FIG. 5 shows a dual calorimeter, which includes a pair of calorimetric reactor assemblies 27 that share a common thermostated wall 31, as shown. The measuring thermopiles 26 in FIGS. 3–5 are used as sensors to detect the temperature difference between the respective cells 12 and the surrounding thermostated block 30. The compensating thermopiles 28 produce Peltier heat as part of a feedback control mechanism for compensating the heat effects arising from the mixing of the reagents, as will be described in conjunction with FIG. 6. Conventional semiconductor thermopiles having 64 junctions and an area of approximately 11.5×9.2 mm² are preferably used.

FIG. 6 is a schematic view of the differential titration calorimetric assembly 100 of the present invention. From FIG. 6, it can be appreciated that the operation, sequence of jet pulses, and the duration and speed of jet pulses from injectors 20 and 22, can all be controlled by a data processor, preferably in the form of a computer 40.

Upon injection of one reagent into the cell, the concentration of the other reagent in the cell decreases. The concentration of both reagents in the cell is known at all times by the computer 40, which takes this into account during calculation of the heat of reaction.

In order to shorten the instrument response time, the heat effects are compensated by the Peltier heat produced by the compensating thermopiles 28 so as to maintain the cell 12 at a generally constant temperature throughout operation. The compensating Peltier heat is controlled by the computer 40 in accordance with the signals received from the measuring thermopile 26. More specifically, the measuring thermopiles 26 generate measuring signals as a function of the temperature difference between the respective cell 12 and the surrounding thermostated block. The measuring signals are amplified by amplifiers 21, as shown in FIG. 6, and received by computer 40, which in turn generates compensation signals proportionally based on the measuring signals. The compensation signals are received by the compensating thermopiles 28, which utilize the compensation signals to generate electric cooling or heating power to maintain the cells 12 at a generally constant temperature. This compensation is accomplished by Peltier heat produced by the compensating thermopile rather than by electric heaters, because the heat of mixing might be positive or negative. The amount of heating or cooling effectuated by the compensating thermopile is controlled by the computer 40, which accomplishes such control simply by regulating the magnitude and direction of current travelling to the compensation thermopile.

The use of additional or supplemental heating of cells by electric heaters is done in other types of titration microcalorimeters, in which cells have a somewhat higher temperature than the thermostat and can be cooled by decreasing the heating current. However, use of such electric heaters is not preferable in the jet-titration microcalorimeter of the present invention, because the Joule effects are compensated individually for each cell, and, as such, the calorimetric cells and all their surroundings should have the same temperature. When the calorimeter operates in the compensation mode, the heat effects of the reaction are recorded as the energy of compensation, which is the energy required to maintain the cell at the predetermined constant temperature.

Use of the device will now be described. The initial filling of the cell with the first reagent is accomplished via injection device 22 and tangential inlet tube 16. The first reagent sits in the cell waiting to be mixed with the second reagent, which is subsequently, rapidly introduced into the cell via injection device 20 and radial inlet tube 14.

Because the second reagent is injected into cell 12 in a very rapid, short pulse (e.g, of 1–2 microliters) via injection device 20 and radial inlet tube 14, the first reagent initially in the cell is displaced very rapidly from the cell through the outlet tube 18 before any substantial mixing between the reagents can occur. As a result, the composition of the initial mixture within the cell can be very precisely estimated. This is in contrast with conventional, slow injection titration methods (i.e., with a time constant slower than the mixing time) which result in a continuously varying composition of the liquid that leaves the reaction cell.

Immediately after or simultaneously with the initial mixing of reagents by injection of the second reagent into the cell 12, a predetermined additional amount of the first reagent (e.g., approximately 10–20 microliters) is injected into the cell 12 via injection device 22 and tangential inlet tube 16 to obtain complete and efficient turbulent stirring of reagents. Of course, this reduces the concentration of the second reagent within the cell 12, and this is taken into account by computer 40 when calculating the heat of reaction. As an alternative method, no additional amount of first reagent is injected into the cell after the initial mixing, but instead, the injection device 22 withdraws a predetermined amount of mixed solution from the cell via tangential inlet tube 16 and then reinjects this predetermined amount of solution back into the cell to cause a turbulent, circular stirring of mixed reagents within the cell.

Irrespective of whether an additional amount of the first reagent is introduced into the cell, after the initial mixing and subsequent turbulent stirring of reagents, it might be preferable to perform a number of additional stirring operations by successive withdrawal and reinjection of the mixed reagents via tangential inlet tube 16 in order to expedite complete mixing.

With each withdrawal and reinjection by tangential inlet tube 16, it may also be desirable to inject an additional amount (e.g., 1–2 microliters) of the second reagent into the cell 12 via radial inlet tube 14. It can be appreciated that, in this instance, the concentration of the second reagent within the cell increases with each injection. As described above, because both injection devices 20 and 22 are computer controlled by computer 40, the exact amount of each reagent within the cell 12 is known at all times and is taken into account during the heat of reaction calculation.

To measure the heat effect of titration using a single cell calorimeter, it is necessary to know the heat of injection (the Joule heat) as well as the heat of dilution of the reagents. This is usually accomplished by measuring the effects of an injection and mixing operation identical in every respect to what has been described above except that, rather than using the complete second reagent, only the solvent of the second reagent is used as a reference liquid. This reference liquid is devoid of the molecular component of the second reagent which causes the full heat of reaction to occur. This heat effect of mixing the reference liquid into the first reagent is memorized in the computer 40. Then the heat effect of mixing the first and second titrating reagents is measured and recorded in the computer. The heat of reaction of mixing the reagents corresponds to the difference of the heat effects of mixing the first and second reagents and the mixing of the first reagent with the reference liquid.

To measure the heat effect of titration using a dual differential calorimeter, one should simultaneously mix the first reagent and the reference liquid in one of the cells and the first and second reagents under study in the other cell, and then record the differential heat effect. This differential heat effect corresponds directly to the heat of reaction.

The magnitude of mechanical heat effects were evaluated by injecting 3 to 20 microliters of water into a single cell filled with water. The injection rate used was 80 microliters per second, which corresponds to a jet speed of 4.8 m/sec. The heat effect is very reproducible and ranges between 1.8 and 12.4 micro Joules, respectively.

The heat effect of mechanical work at the time of injection (Joule heat) was also evaluated by measuring the differential heat effect obtained upon the simultaneous injection of the same amount of water, 3 micro liters, in both cells of the dual microcalorimeter. This differential heat effect is much smaller than the effect of injection of water into one cell alone, i.e., the heat effect of injection in two cells are almost equal and compensate each other. The small difference between these effects is highly reproducible and can be easily decreased almost to zero by small adjustments in the speed and/or volume of jets in each of the cells.

In another experiment, one of the calorimeter cells was filled with 0.5M GdmCl (volume 0.3 ml), and, at predetermined times, 5 micro-liters of water were injected. The reference cell was filled with water, and similar 5 micro-liter injections of water were made. Under these conditions, the observed heat effect of injection, i.e., the difference of the two Joule heats of mixing, was very small. It did not exceed 1% of the heat of mixing GdmCl with water and could be easily taken into account in order to obtain the heat of reaction.

Figure 7:
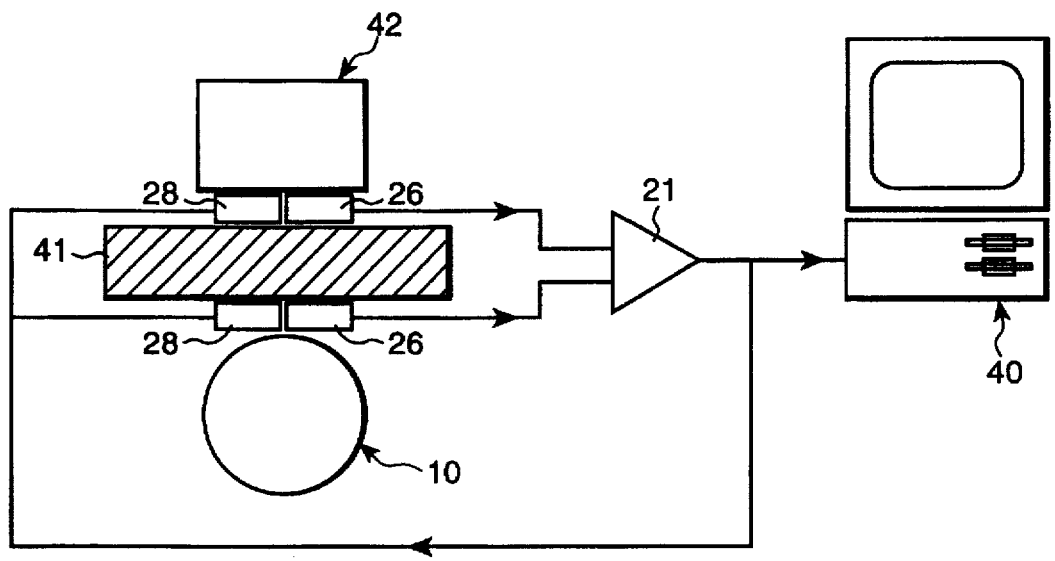
FIG. 7 is a schematic representation of a computer-controlled differential titration calorimetric assembly in accordance with the principles of the present invention in which two different types of reactors share the same thermostated block.

FIG. 7 is a schematic representation of a differential titration calorimeter, in accordance with the principles of the present invention, wherein two different types of reactors are provided and share a common thermostated block 41. More specifically, for example, in FIG. 7 a jet-type calorimetric reactor 10 as described hereinbefore is provided as one reactor, while a conventional Flow-Mix calorimetric reactor 42 is provided as the other reactor. Using a combination of two functionally different cells with the same thermostated block eliminates the need for using a separate reference cell. That is, in this arrangement, each cell can be used as the reference cell of the other.

Figure 8:
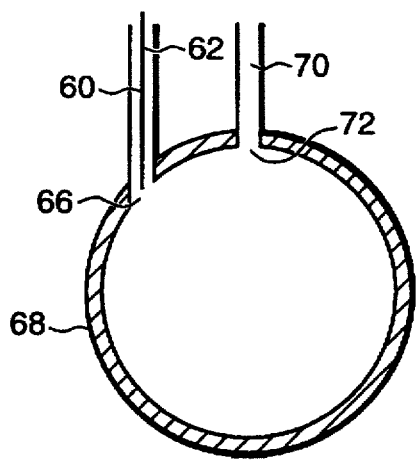
FIG. 8 is a sectional front view of another embodiment of the reaction cell in accordance with the principles of the present invention.
Figure 9:
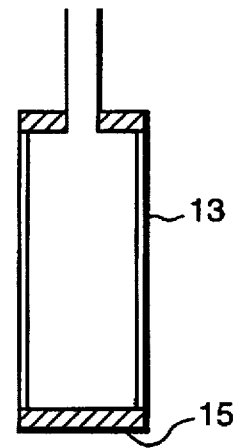
FIG. 9 is a sectional side view of the embodiment of the reaction cell of the present invention shown in FIG. 8.

In addition, in another embodiment shown in FIGS. 8 and 9, the two inlet tubes 60 and 62 are both tangentially disposed with respect to the cell 64, and are removably inserted into an opening 66 in the rim 68. Similarly, the outlet tube 70 is removably inserted into an opening 72 in the rim 68. The removability of the inlet tubes 60, 62 and outlet tube 70 lends flexibility to the assembly and facilitates cleaning of the cell 64 and tubes. The tubes 60 and 62 are preferably welded to one another and are inserted into the same hole 66 in the rim 68. It will also be noted that all three tubes 60, 62, and 70 are received by the rim 68 towards the top of the cell 64, which allows the cell to be easily immersed in a water bath. In this embodiment, such a water bath can be used in place of the thermostated block, as can be appreciated by those skilled in the art. The embodiment shown in FIGS. 8 and 9 can function similarly to the embodiment shown in FIGS. 1 and 2, with the first and second reagents both being injected tangentially into the cell.

Figure 10:
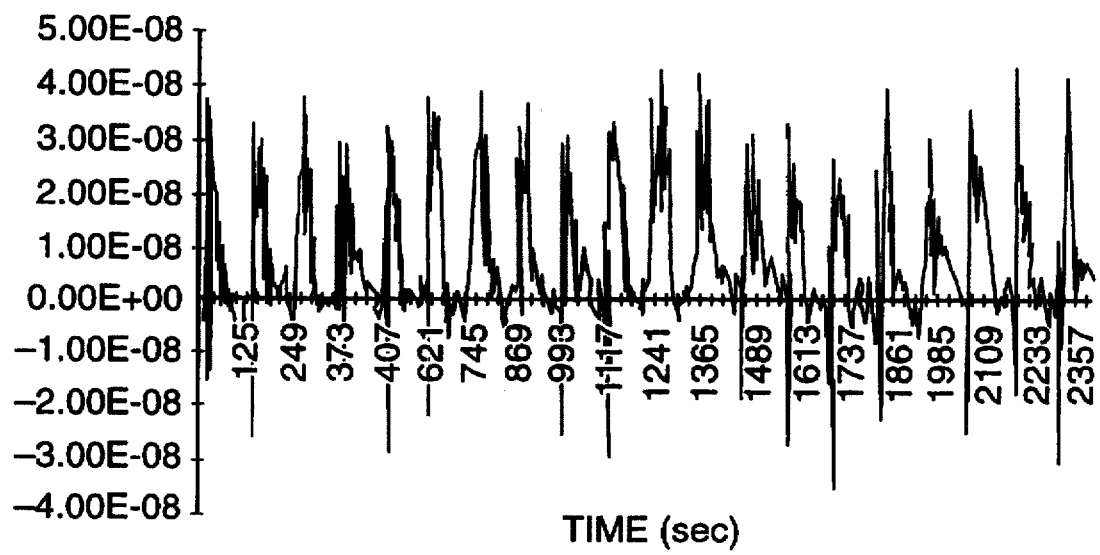
FIG. 10 shows the output in volts of 5 micro Joules electrical calibration pulses applied together with mixing pulses using the tween differential calorimetric cell assembly of the present invention.
Figure 11:
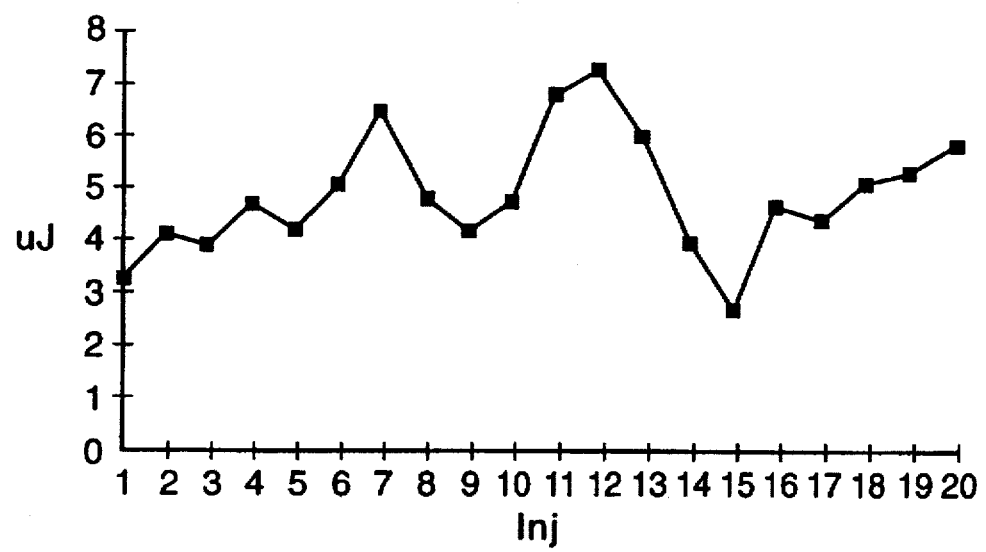
FIG. 11 is a graphical representation showing the energy of the mixing pulses used in the results shown in FIG. 10.

FIG. 10 shows the instrument output in volts plotted over time in an experiment in which 5 micro-Joules of electrical calibration pulses were applied along with mixing pulses. In FIG. 10, the baseline energy attributable to the heat effects of the mechanical mixing has been subtracted. FIG. 11 shows the measured energy of the pulses. The standard derivation for this experiment was 1.16 micro-Joules.

Figure 12:
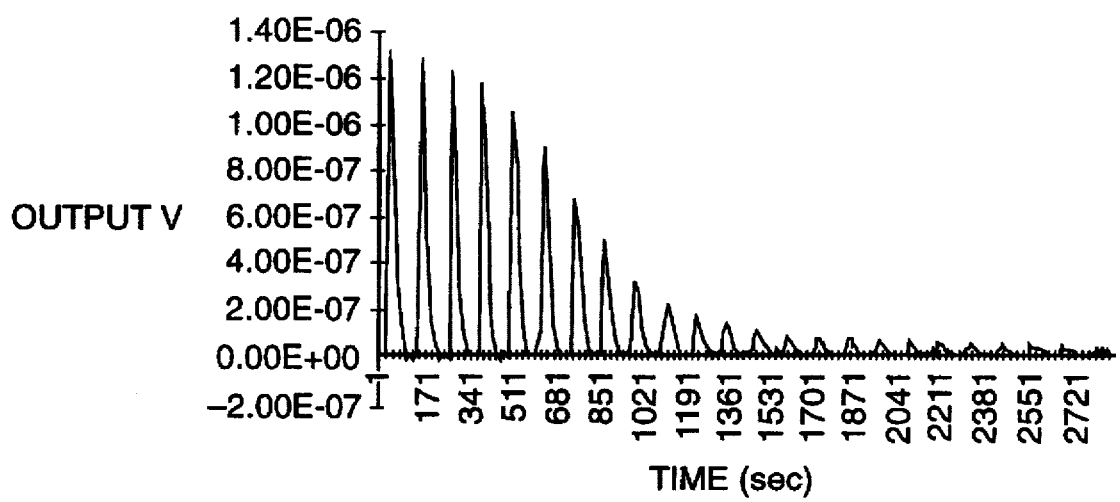
FIG. 12 is a graphical representation of the experimental results of the titration of pancreatic ribonuclease A (RNase) by cyclic monophosphate.
Figure 13:
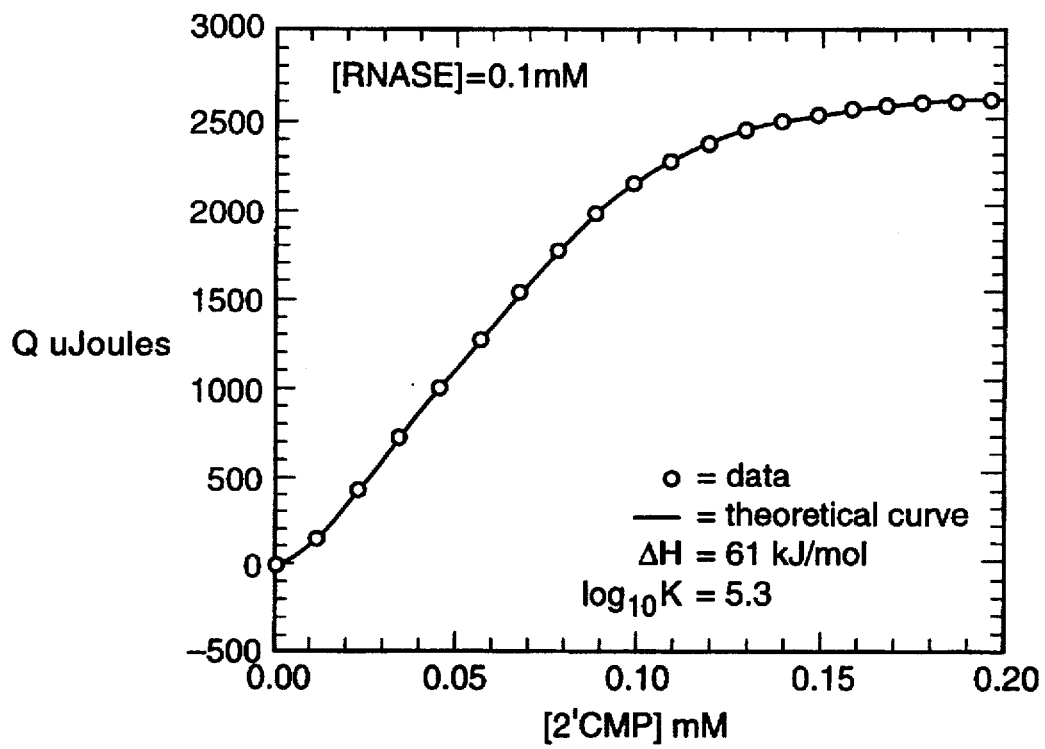
FIG. 13 is a graphical representation of the cumulative heat of reagent binding by protein in the experimental results shown in FIG. 12.

FIG. 12 shows biochemical experimental results of titration of ribonuclease A (RNase) by cyclic monophosphate (2'CMP). The concentration of Rnase in the calorimetric cell was $1.01 \times 10^{-4}$M, and the concentration of 2'CMP was $1.0 \times 10^{-3}$M. The volume of the calorimetric cell was 0.438 mL, and the reagent 2'CMP was injected in 5 micro-liter portions. The cumulative heat of reagent binding by protein is shown in FIG. 13.

It thus will be seen that the objects of this invention have been fully and effectively accomplished. It will be realized, however, that the foregoing specific preferred embodiments have been shown and described for illustrative purposes only, and that the present invention is subject to change without departure from its principles. Therefore, this invention includes all modifications encompassed by the spirit and scope of the following claims.

What is claimed is:

1. A method for measuring the heat of reaction resulting from the mixture of a plurality of liquid reagents comprising the steps of:

provided a first liquid reagent into a compartment;

providing a second liquid reagent into said compartment so as to mix said second reagent with said first reagent within said compartment;

withdrawing a predetermined amount of the mixed first and second reagents from the compartment;

depositing the withdrawn predetermined amount of the mixed first and second reagents back into the compartment;

generating electrical signals based on the heat of reaction of the mixed first and second reagents; and deriving data indicative of the heat of reaction based on said electrical signals.

2. The method according to claim 1, further comprising:
displacing a portion of the first liquid reagent from said compartment when said second liquid reagent is provided into said compartment.

3. The method according to claim 2, further comprising:
utilizing a data processor to receive the electrical signals based on the heat of reaction and to generate output signals proportional to the heat of reaction;
utilizing said output signals to maintain said compartment at a generally constant temperature during mixture of said first and second reagents; and
wherein said deriving of data indicative of the heat of reaction based on the electrical signals is accomplished by determining a magnitude of the output signals required to maintain the compartment at said generally constant temperature.

4. A method according to claim 2, wherein said compartment has a substantially cylindrical shape, and wherein the depositing of the mixed first and second liquid reagents back into the compartment is done generally tangentially to said cylindrical compartment so as to cause the first and second reagents to circulate in a generally uniform direction within the compartment so as to facilitate complete mixture of said first and second reagents.

5. A method according to claim 1, further comprising repeating the withdrawing and depositing steps at least one additional time to accomplish further stirring of the reagents.

6. A method for measuring the heat of reaction resulting from the mixture of a plurality of liquid reagents comprising:
filling a compartment with a first liquid reagent;
providing a second liquid reagent into said compartment to cause a portion of said first liquid reagent to be displaced from said compartment;
withdrawing a predetermined portion of the first and second reagents from the compartment after said portion of the first liquid reagent is displaced from said compartment;
depositing the withdrawn predetermined portion of first and second reagents back into the compartment;
generating electrical signals based on the heat of reaction resulting from mixture of the first and second reagents; and
deriving data indicative of the heat of reaction based on said electrical signals.

7. A method for measuring the heat of reaction resulting from the mixture of a plurality of reagents comprising the steps of:
initially providing a predetermined amount of first reagent into a compartment;
then providing a predetermined amount of second reagent into said compartment to cause said first and second reagents to mix within said compartment;
then providing an additional amount of said first reagent into the compartment in such fashion which causes the mixed reagents within the compartment to circulate in a substantially uniform direction within the compartment;
generating electrical signals based on the heat of reaction of the mixed reagents within the compartmentp; and deriving data indicative of the heat of reaction based on said electrical signals.

8. A method according to claim 7, wherein the compartment has a substantially circular cross-section through a predetermined plane, and wherein the step of providing an additional amount of said first reagent into the compartment is accomplished by tangentially injecting a stream of said first reagent relative to said circular cross-section so as to cause the mixed reagents within the cell to circulate in said substantially uniform direction within the cell.

9. A method according to claim 7, further comprising the steps of
providing an additional amount of said second reagent into the compartment substantially simultaneously with providing the additional amount of said first reagent into the compartment.

10. A method according to claim 7, further comprising the step of calculating the relative concentrations of said first and second reagents within said compartment in order to derive said heat of reaction.

11. A method according to claim 7, further comprising the steps of withdrawing a predetermined portion of the first and second reagents after they are mixed within said compartment and depositing the withdrawn predetermined portion of mixed reagents back into said compartment.

12. A device for measuring the heat of reaction resulting from mixture of a plurality of reagents, comprising:
a compartment;
a first injection assembly for providing a first reagent into said compartment;
a second injection assembly for providing a second reagent into said compartment to permit said first and second reagents to initially mix within said compartment,
at least one of said first and second injection assemblies being constructed and arranged to be able to i) withdraw a predetermined portion of said first and second reagents from said compartment after the reagents have been initially mixed within said compartment and ii) deposit the withdrawn predetermined portion of said first and second reagents back into the compartment so as to facilitate stirring of said first and second reagents within said compartment; and
a measuring apparatus operably connected with said compartment for deriving data indicative of the heat of reaction resulting from mixing said first and second reagents.

13. A device according to claim 12, wherein said compartment is generally cylindrical in shape, and wherein said at least one of the injection assemblies comprises a first injection device and a tangential inlet tube providing a passage between said first injection device and said compartment, said tangential inlet tube being constructed and arranged to direct the deposited predetermined portion of said first and second reagents in a generally circumferential direction within said cylindrical compartment.

14. A device according to claim 13, wherein one of the injection assemblies comprises said first injection device and said tangential inlet tube, and wherein another one of said injection assemblies comprises a second injection device and a radial inlet tube providing a passage between said second injection device and said compartment, said radial inlet tube being constructed and arranged to direct the second reagent towards the center of said compartment when said second reagent is provided into said compartment by said second injection device.

15. A device according to claim 14, further comprising an outlet tube connected with said compartment for permitting a portion of the first reagent to be displaced from the compartment therethrough when said second reagent is provided into said compartment by the first injection device to permit the reagents to initially mix.

16. A device according to claim 12, wherein said measuring apparatus comprises a measuring thermopile connected with said compartment for generating a measuring signal indicative of the heat of reaction resulting from the mixture of said reagents, and a data processor for processing said measuring signal to derive said data indicative of the heat of reaction.

17. A device according to claim 16, wherein said measuring apparatus further comprises a compensating thermopile structurally connected with said compartment and electrically connected with said data processor for receiving compensation signals from said data processor based on said measuring signals and for converting said compensation signals into electric power used to maintain said compartment at a generally constant temperature during the heat of reaction.

18. A device according to claim 12, wherein said injection assemblies comprise automatic syringe injectors electrically connected with said measuring apparatus.

* * * * *

UNITED STATES PATENT AND TRADEMARK OFFICE
CERTIFICATE OF CORRECTION

PATENT NO. : 5,707,149
DATED : January 13, 1998
INVENTOR(S) : Freire, et. al.

It is certified that error appears in the above-indentified patent and that said Letters Patent is hereby corrected as shown below:

At column 1, line 5:

--ORIGINATION OF THE INVENTION

The work that resulted in the subject invention was supported by NIH Grant No. RR 04328, with the National Institute of Health as the sponsoring government agency.-- should be inserted.

Signed and Sealed this

Twenty-fifth Day of August, 1998

Attest:

Attesting Officer

BRUCE LEHMAN

Commissioner of Patents and Trademarks